(12) United States Patent
Kabra

(10) Patent No.: US 8,785,497 B2
(45) Date of Patent: Jul. 22, 2014

(54) AQUEOUS OPHTHALMIC COMPOSITIONS CONTAINING ANIONIC THERAPEUTIC AGENTS

(75) Inventor: Bhagwati P. Kabra, Euless, TX (US)

(73) Assignee: Alcon Research, Ltd., Forth Worth, TX (US)

( * ) Notice: Subject to any disclaimer, the term of this patent is extended or adjusted under 35 U.S.C. 154(b) by 89 days.

(21) Appl. No.: 12/759,803

(22) Filed: Apr. 14, 2010

(65) Prior Publication Data

US 2010/0266713 A1    Oct. 21, 2010

Related U.S. Application Data

(60) Provisional application No. 61/170,397, filed on Apr. 17, 2009.

(51) Int. Cl.
*A61K 31/195*    (2006.01)
*A61K 31/277*    (2006.01)

(52) U.S. Cl.
USPC .......................... 514/564; 514/771; 424/721

(58) Field of Classification Search
USPC .................................. 514/567, 771; 424/721
See application file for complete search history.

(56) References Cited

U.S. PATENT DOCUMENTS

| | | | |
|---|---|---|---|
| 3,931,319 A | 1/1976 | Green et al. | |
| 4,027,020 A | 5/1977 | Green et al. | |
| 4,407,791 A | 10/1983 | Stark | |
| 4,525,346 A | 6/1985 | Stark | |
| 4,836,986 A | 6/1989 | Ogunbiyi et al. | |
| 5,037,647 A | 8/1991 | Chowhan et al. | |
| 5,110,493 A | 5/1992 | Cherng-Chyi et al. | |
| 5,300,287 A | 4/1994 | Park | |
| 5,653,972 A * | 8/1997 | Desai et al. | 424/78.04 |
| 5,886,030 A | 3/1999 | Maniar | |
| 2002/0098160 A1 | 7/2002 | Chowhan et al. | |
| 2005/0080107 A1* | 4/2005 | Ochiai et al. | 514/317 |
| 2010/0035894 A1 | 2/2010 | Sawa | |

FOREIGN PATENT DOCUMENTS

| | | |
|---|---|---|
| CA | 2666440 | 4/2008 |
| EP | 2078527 | 7/2009 |
| JP | 9503791 | 4/1997 |
| WO | 91/09523 | 7/1991 |
| WO | 9321903 A1 | 11/1993 |
| WO | 98/52579 | 11/1998 |
| WO | 2005/053672 | 6/2005 |
| WO | 2008/044733 | 4/2008 |
| WO | 2009/111170 | 9/2009 |
| WO | 2009/126682 | 10/2009 |

OTHER PUBLICATIONS

Corresponding International Application No. PCT/US2010/030979 PCT International Search Report with mailing date Jun. 25, 2010.
Corresponding International Application No. PCT/US2010/030979 PCT Written Opinion with mailing date Jun. 25, 2010.

* cited by examiner

*Primary Examiner* — Zohreh Fay
(74) *Attorney, Agent, or Firm* — Scott A. Chapple

(57) ABSTRACT

The present invention is directed to the provision of multi-dose, ophthalmic compositions. The compositions possess sufficient antimicrobial activity to satisfy USP preservative efficacy requirements, as well as similar preservative standards (e.g., EP and JP). The compositions include a balance of ingredients that allow for the formation of ophthalmic compositions that include an anionic drug and exhibit desired characteristics such as stability, preservation efficacy, desired pH, desired osmolality, combinations thereof or the like.

24 Claims, 2 Drawing Sheets

AQUEOUS OPHTHALMIC COMPOSITIONS CONTAINING ANIONIC THERAPEUTIC AGENTS

CROSS-REFERENCE TO RELATED APPLICATION

This application claims priority under 35 U.S.C. §119 to U.S. Provisional Patent Application No. 61/170,397, filed Apr. 17, 2009, the entire contents of which are incorporated herein by reference.

TECHNICAL FIELD OF THE INVENTION

The present invention is related to an aqueous ophthalmic composition that includes an anionic therapeutic agent and exhibits clarity, physical stability, preservation efficacy, desired osmolality, desired pH or any combination thereof. More specifically, the present invention relates to an aqueous ophthalmic solution that include an anionic phosphodiesterase enzyme (PDE-4) inhibitor such as cilomilast and exhibit clarity, stability, preservation efficacy, desired osmolality, desired pH or any combination thereof.

BACKGROUND OF THE INVENTION

The present invention is directed to ophthalmic compositions that include an anionic drug. The ophthalmic compositions are formulated so as to have sufficient antimicrobial activity to satisfy the preservation efficacy requirements of the United States Pharmacopeia ("USP") and/or analogous guidelines in other countries. In addition to preservation efficacy, the compositions will typically exhibit one or more other desirable attributes such as stability, desired pH, clarity, desired osmolality, combinations thereof or the like. The ability to achieve preservation and any other desired attributes is based on a unique combination of formulation ingredients that allow a greater amount of tonicity or osmolality enhancing agent and/or a lower amount of antimicrobial preservative or preservative aid to be present in the composition while still maintaining preservation efficacy.

Ophthalmic compositions that are utilized multiple times by a patient are often referred to as being of a "multi-dose" nature. Such compositions can be manufactured under sterile conditions via procedures that are well known to those skilled in the art. However, once the packaging for a product is opened, such that the composition contained therein is exposed to the atmosphere and other sources of potential microbial contamination (e.g., the hands of a human patient), the sterility of the product may be compromised.

Due to the frequent, repeated exposure of multi-dose products to the risk of microbial contamination, it is necessary to employ a means for preventing such contamination from occurring. The means employed may be: (i) a chemical agent that prevents the proliferation of microbes in a composition, which is referred to herein as an "antimicrobial preservative"; or (ii) a packaging system that prevents or reduces the risk of microbes reaching a pharmaceutical composition within a container.

Prior multi-dose ophthalmic compositions have generally contained one or more antimicrobial preservatives in order to prevent the proliferation of bacteria, fungi and other microbes. Such compositions may come into contact with the cornea either directly or indirectly. The cornea is particularly sensitive to exogenous chemical agents. Consequently, in order to minimize the potential for harmful effects on the cornea, it is preferable to use anti-microbial preservatives that are relatively non-toxic to the cornea, and to use such preservatives at relatively low concentrations.

A desired balance between anti-microbial efficacy and potential toxicological effects of anti-microbial preservatives is often difficult to achieve. More specifically, the concentration of an antimicrobial agent necessary for the preservation of ophthalmic formulations from microbial contamination may create the potential for toxicological effects on the cornea and/or other ophthalmic tissues. Using lower concentrations of the anti-microbial agents generally helps to reduce the potential for such toxicological effects, but the lower concentrations may be insufficient to achieve the required level of biocidal efficacy (i.e., antimicrobial preservation).

The use of an inadequate level of antimicrobial preservation may create the potential for microbial contamination. Such contamination is typically undesirable for most biological systems and particularly undesirable for the human eye.

This balance is further complicated in situations where it is desirable to deliver an anionic therapeutic agent using a multi-dose ophthalmic composition. Preservation agents commonly used for ophthalmic compositions are often positively charged within the composition, particularly when that composition is an aqueous solution. In turn, these agents often interact with anionic drugs in an undesirable manner, which can result in instability of the composition, lack of preservation efficacy, lack of therapeutic efficacy, combinations thereof or the like.

Prior attempts to address these undesirable interactions typically involved the addition of a surfactant to the composition (see U.S. Pat. No. 5,110,493, which is fully incorporated herein by reference for all purposes). However, the addition of surfactant to an ophthalmic composition is often undesirable. Surfactants can add significant expense to the composition. Moreover, as a general rule, it is often undesirable to add further ingredients to an ophthalmic composition where the addition of those ingredients can potentially be avoided.

Thus, there exists a need for ophthalmic compositions that include anionic drugs and still exhibit desirable attributes such as preservation efficacy, stability, desired pH, clarity, desired osmolality, combinations thereof or the like. Moreover, it would be desirable to avoid the use of surfactant or at least lower amounts of surfactant in the composition.

SUMMARY OF THE INVENTION

Accordingly, the present invention is directed to an aqueous ophthalmic composition. The composition includes an anionic therapeutic agent. The composition includes a polyol (e.g., mannitol) that is preferably at a concentration that is at least 0.05 w/v % but is preferably no greater than 1.5 w/v %. The composition includes borate at a concentration that is preferably at least 0.1 w/v % but is preferably no greater than 0.5 w/v %. The composition includes osmolality enhancing agent wherein the osmolality enhancing agent raises the osmolality of the overall composition at least 160 mOsm/Kg relative to a control composition that includes the exact same ingredients as the overall composition with the exception that the osmolality enhancing agent is replaced with water. The osmolality enhancing agent is preferably present in the composition at a concentration that is at least 70 mmol and more typically at least 90 mmol. The osmolality enhancing agent also typically enhances the physical stability of the drug. The osmolality of the composition is preferably in the range of 240 to 360 mOsm/kg.

BRIEF DESCRIPTION OF THE DRAWINGS

The accompanying drawings, which are incorporated in and constitute a part of this specification, illustrate aspects of the invention and together with the description, serve to explain the principles of the invention.

DETAILED DESCRIPTION OF THE INVENTION

Figure 1:
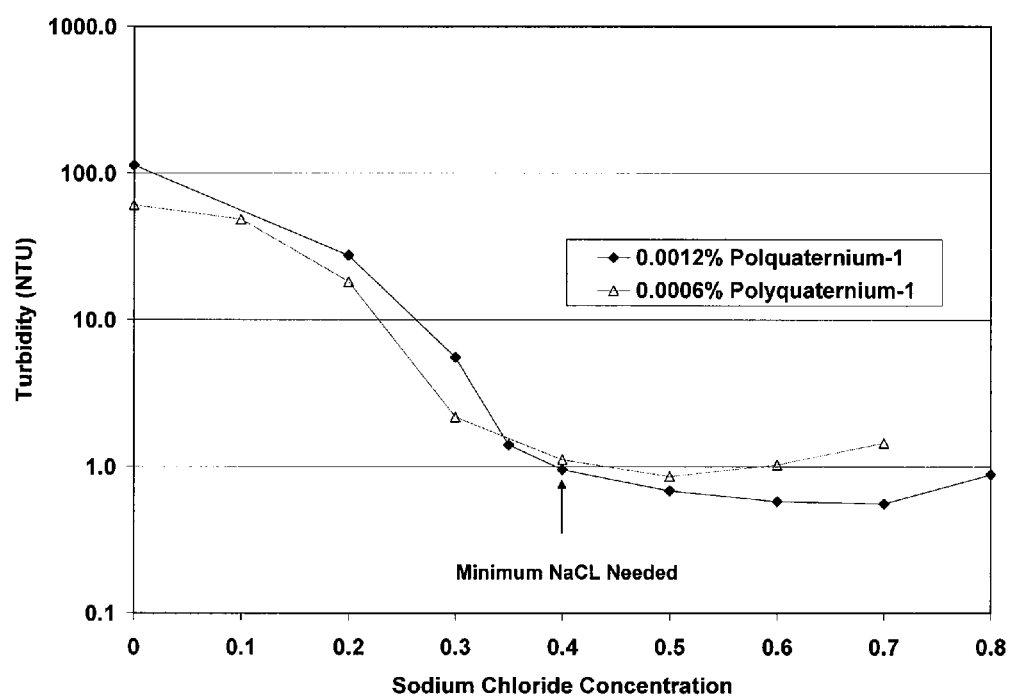
FIG. 1 is a chart showing level of turbidity for ophthalmic composition that include various amounts of sodium chloride in the presence of 0.22 w/v % cilomilast, 0.3 w/v % boric acid, 0.1 w/v % mannitol, 0.0006 w/v % or 0.0012 w/v % polyquaternium-1 with pH adjusted to 7.6 with sodium hydroxide.

The present invention is predicated upon the provision of an ophthalmic composition, particularly an aqueous ophthalmic solution, that includes an anionic therapeutic agent as well as an aqueous vehicle that is particularly suitable for delivery of such agent. The ophthalmic composition exhibits stability, clarity, preservation efficacy, desired osmolality, desired pH or any combination thereof. Such characteristics are achieved within the solution through a carefully balanced combination of three, four, five or all of an osmolality enhancing agent, borate, polyol, preservative, pH adjusting agent and therapeutic agent in water.

Unless otherwise indicated, percentages provided for the ingredients of the ophthalmic composition of the present invention are weight/volume (w/v) percentages.

The composition includes at least one and potentially multiple anionic therapeutic agents. As used herein, an anionic therapeutic agent is any therapeutic agent that includes an acidic group and exhibits a negative charge in solution at a pH of about 5 to about 9 and more preferably about 6 to about 8. In one preferred embodiment, the anionic therapeutic agent includes one or more carboxylic acid groups for exhibiting the negative charge. Examples of suitable anionic therapeutic agents include, without limitation, anionic PDE-4 inhibitors suprofen, diclofenac, ketorolac, combinations thereof or the like. One particularly preferred anionic therapeutic agent for which the vehicle of the present invention is particularly desirable is cilomilast.

The present invention can be directed to the provision of multi-dose ophthalmic compositions in connection with the treatment of conditions wherein the cornea or adjacent ocular tissues are irritated, or conditions requiring frequent application of a composition, such as in the treatment of dry eye patients. The compositions of the present invention can be useful in the field of artificial tears, ocular lubricants, and other compositions used to treat dry eye conditions, as well as other conditions involving ocular inflammation or discomfort. One particular anionic therapeutic agent, cilomilast, has exhibited desirable efficacy in the treatment of dry eye. Thus, the composition of the present invention, particularly when it includes cilomilast, can be administered, for example as drops, to the human eye as treatment for dry eye. The composition of the present invention can also be used to treat ocular allergies. The use of the vehicle of the present invention for cilomilast containing solutions is particularly advantageous since cilomilast can be particularly difficult to stabilize in solution.

The composition of the present invention typically includes at least about 0.001 w/v % and more typically at least about 0.01 w/v % anionic therapeutic agent. The composition also typically includes no greater than about 1.0 w/v % and more typically no greater than about 0.5 w/v % anionic therapeutic agent. When cilomilast is included in the composition, it will typically be at least 0.01 w/v % and even more typically at least 0.05 w/v % of the composition and will typically be no greater than 0.4 w/v % and even more typically no greater than 0.3 w/v % and even possibly no greater than about 0.22 w/v % of the composition.

The composition of the present invention can potentially also include one or more additional therapeutic agents that can be used in conjunction with the one or more anionic therapeutic agents. Generally, and without limitation, such additional therapeutic agents suitable for the composition include: anti-glaucoma agents, anti-angiogenesis agents; anti-infective agents; anti-inflammatory agents; growth factors; immunosuppressant agents; and anti-allergic agents. Anti-glaucoma agents include beta-blockers, such as betaxolol and levobetaxolol; carbonic anhydrase inhibitors, such as dorzolamide; prostaglandins, such as travoprost, bimatoprost, and latanoprost; seretonergics; muscarinics; dopaminergic agonists. Anti-angiogenesis agents include receptor tyrosine kinase inhibitors. Growth factors include EGF or VEGF. Anti-allergic agents include olopatadine, emadestine, cetrizine, ketotifen and epinastine. Anti-infective agents include moxifloxacin and gatifloxacin.

The ophthalmic drug may be present in the form of a pharmaceutically acceptable salt.

The ophthalmic composition also includes osmolality enhancing agent. The osmolality enhancing agent can be comprised of salts, weak bases, combinations thereof or the like. The osmolality enhancing agent will typically contribute as at least 140 mOsm/Kg, more typically at least 160 mOsm/Kg and even more typically at least 180 mOsm/Kg to the overall osmolality of the ophthalmic composition. In such embodiments, the ophthalmic composition will typically have an osmolality that is at least at least 140 mOsm/Kg, more typically at least 160 mOsm/Kg and even more typically at least 180 mOsm/Kg greater than an osmolality of a control composition that includes the exact same ingredients as the ophthalmic composition with the exception that the osmolality enhancing agent is replaced with water and pH is brought to the same value as that of the ophthalmic composition by using sodium hydroxide or hydrogen chloride if necessary. In one preferred embodiment, the osmolality enhancing agent is comprised of, consists essentially of or consists of sodium citrate, sodium sulfate, sodium chloride, potassium chloride, tromethamine or any combination thereof. In a highly preferred embodiment, the osmolality enhancing agent is comprised of, consists essentially of or consists of sodium chloride, potassium chloride, tromethamine or any combination thereof. In a particularly preferred embodiment, the osmolality enhancing agent is substantially entirely (i.e., at least 70% by weight) or entirely sodium chloride.

The composition of the present invention typically includes at least about 70 mmol, more typically at least 80 mmol, still more typically at least about 90 mmol and even possibly at least about 110 mmol osmolality enhancing agent. The composition typically includes no greater than about 250 mmol and more typically no greater than about 200 mmol and still more typically no greater than about 180 mmol osmolality enhancing agent. When the osmolality enhancing agent is substantially entirely (i.e., at least 70% by weight) or entirely sodium chloride, the composition will typically include at least 50 mmol and even more typically at least 85 mmol sodium chloride and even possibly at least about 100 mmol sodium chloride. The composition will typically include no greater than 250 mmol and even more typically no greater than 200 mmol and still more typically no greater than 180 mmol sodium chloride.

The composition of the present invention will also typically include borate and polyol. As used herein, the term "borate" shall refer to boric acid, salts of boric acid, borate derivatives and other pharmaceutically acceptable borates, or combinations thereof. Most suitable are: boric acid, sodium borate, potassium borate, calcium borate, magnesium borate, manganese borate, and other such borate salts. As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol. Mannitol is a particularly preferred polyol as is illustrated in the examples included herein. As such, in a preferred embodiment, the polyol of the composition is entirely or substantially entirely (i.e., at least 70% by weight) mannitol.

As is known, borate interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. It shall be understood that weight/volume percentages of the ingredients polyol and borate include those amounts whether as part of a complex or not.

Polyol is typically at least 0.005 w/v %, more typically at least 0.05 w/v % and even possibly at least 0.09 w/v % of the composition. Polyol is typically no greater than 2.0 w/v %, more typically no greater than 1.0 w/v % and even possibly no greater than 0.2 w/v % of the composition. In a preferred embodiment, the polyol includes or is entirely or substantially entirely mannitol and the amount of mannitol is at least 0.03 w/v %, more typically at least 0.07 w/v % and even possibly at least 0.09 w/v % of the composition and is typically no greater than 1.5 w/v %, more typically no greater than 1.0 w/v % and even possibly no greater than 0.13 w/v % of the composition.

Borate, particularly when the borate is entirely or substantially entirely boric acid, is typically at least 0.05 w/v %, more typically at least 0.18 w/v % and even possibly at least 0.27 w/v % of the composition and is typically no greater than 1.0 w/v %, more typically no greater than 0.5 w/v %, still more typically no greater than 0.4 w/v % and even possibly no greater than 0.35 w/v % or 0.33 w/v % of the composition.

The compositions of the present invention typically include a preservative. Potential preservatives include, without limitation, hydrogen peroxide, chlorine containing preservatives such as benzalkonium chloride or others. According to a preferred aspect, however, the ophthalmic composition of the present invention is substantially free of any chloride containing preservatives and, particularly, is substantially free of benzalkonium chloride. Most preferred preservatives included in the ophthalmic composition are polymeric quaternary ammonium compounds.

As used herein, the phrase "substantially free of" as it refers to an ingredient of the ophthalmic composition means that it is contemplated that the ophthalmic solution can be either entirely devoid of that particular ingredient or includes only a nominal amount of that particular ingredient.

The polymeric quaternary ammonium compounds useful in the compositions of the present invention are those which have an antimicrobial effect and which are ophthalmically acceptable. Preferred compounds of this type are described in U.S. Pat. Nos. 3,931,319; 4,027,020; 4,407,791; 4,525,346; 4,836,986; 5,037,647 and 5,300,287; and PCT application WO 91/09523 (Dziabo et al.). The most preferred polymeric ammonium compound is polyquaternium 1, otherwise known as POLYQUAD® or ONAMERM® with a number average molecular weight between 2,000 to 30,000. Preferably, the number average molecular weight is between 3,000 to 14,000.

The polymeric quaternary ammonium compounds are generally used in the compositions of the present invention in an amount that is greater than about 0.00001 w/v %, more typically greater than about 0.0003 w/v % and even possibly greater than about 0.0004 w/v % or even 0.0007 w/v % of the ophthalmic composition. Moreover, the polymeric quaternary ammonium compounds are generally used in the compositions of the present invention in an amount that is less than about 0.01 w/v %, more typically less than about 0.003 w/v %, even more typically less than about 0.0015 w/v % and even possibly less than about 0.0007 w/v % of the ophthalmic composition.

In addition to the above, the compositions of the present invention may also contain various types of pharmaceutical excipients, such as surfactants, viscosity-modifying agents (e.g., hydroxyethyl cellulose (HEC), hydroxypropylmethyl cellulose (HPMC) or a combination thereof) and so on. However, it can also be a desirable advantage of the composition of the present invention to avoid one or all of the aforementioned additional excipients. In one preferred embodiment, the composition of the present invention is substantially free of any surfactant (i.e., includes less than 0.05 w/v % and more preferably less than 0.01 w/v % surfactant) or is entirely free of any surfactant.

Advantageously, the composition of the present invention can exhibit one or a combination of multiple desirable attributes. The composition can employ combinations of polyol (e.g., mannitol), preservative (e.g., polyquaternium-1) and/or borate (e.g., boric acid) at relatively low concentrations while still achieving a high degree of preservation efficacy. In turn, the composition of the present invention is typically exhibits greater biological compatibility with the human eye upon instillation thereon. Moreover, such relatively low concentrations of polyol, preservative and/or borate can often allow for the presence of greater concentrations of osmolality enhancing agents within the composition and such osmolality enhancing agents, particularly sodium chloride, can provide desired and/or needed clarity and physical stability to compositions containing anionic drugs. In particular embodiments, these combinations can avoid turbidity that might otherwise be present in similar compositions. Preferably the turbidity of the composition is less than 3 NTU (nephelometric turbidity units), more typically less than 2 NTU and even possibly less than 1.5 NTU.

The present invention is particularly directed to the provision of multi-dose ophthalmic compositions that have sufficient antimicrobial activity to allow the compositions to satisfy the USP preservative efficacy requirements, as well as other preservative efficacy standards for aqueous pharmaceutical compositions.

The preservative efficacy standards for multi-dose ophthalmic solutions in the U.S. and other countries/regions are set forth in the following table:

Preservative Efficacy Test ("PET") Criteria
(Log Order Reduction of Microbial Inoculum Over Time)

| | Bacteria | Fungi |
|---|---|---|
| USP 31 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |

[1]There are two preservative efficacy standards in the European Pharmacopoeia ' "A" and "B".

The standards identified above for the USP 27 are substantially identical to the requirements set forth in prior editions of the USP.

The compositions of the present invention will generally be formulated as sterile aqueous solutions. The compositions of the present invention are also formulated so as to be compatible with the eye and/or other tissues to be treated with the compositions. The ophthalmic compositions intended for direct application to the eye will be formulated so as to have a pH and tonicity that are compatible with the eye. It is also contemplated that the compositions can be suspensions or other types of solutions.

The compositions will typically have a pH in the range of 4 to 9, preferably 5.5 to 8.5, and most preferably 5.5 to 8.0. Particularly desired pH ranges are 6.0 to 8.0 and more specifically 6.4 to 7.8. When cilomilast is included as the anionic drug, the pH is preferably in the range of 6.8 to 8.0, more preferably 6.8 to 7.9 and even more preferably 7.2 to 7.9. The compositions will typically have an osmolality that is at least 200 milliosmoles per kilogram (mOsm/kg), more typically at least 240 mOsm/kg and even more typically at least 260 mOsm/kg. The compositions will typically have an osmolality that is no greater than 380 mOsm/kg, more typically no greater than 360 mOsm/kg and even more typically no greater than 330 mOsm/kg.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

Table A below provides a listing of exemplary ingredients suitable for an exemplary preferred formulation of the ophthalmic composition of the present invention and a desired weight/volume percentage for those ingredients.

TABLE A

| Ingredient | w/v percent |
|---|---|
| Therapeutic Agent (e.g., Cilomilast) | 0.2 |
| Sodium Chloride | 0.7 |
| Boric Acid | 0.3 |
| Mannitol | 0.1 |
| polymeric quaternary ammonium compound | 0.0005 |
| NaOH/HCl | sufficient to achieve pH = 7.3 |
| purified water | Q.S. 100 |

It is understood that the weight/volume percents in table A can be varied by ±10%, ±20%, ±30%, ±90% of those weight/volume percents or more and that those variances can be specifically used to create ranges for the ingredients of the present invention. For example, an ingredient weight/volume percent of 10% with a variance of ±20% means that the ingredient can have a weight/volume percentage range of 8 to 12 w/v %.

The following examples are presented to further illustrate selected embodiments of the present invention. The formulations shown in the examples were prepared using procedures that are well-known to persons of ordinary skill in the field of ophthalmic pharmaceutical compositions.

EXAMPLES

The formulations of Examples A-Y are provided as an illustration of desirability of the present invention. The examples illustrate the antimicrobial activity and/or preservative efficacy of the ophthalmic compositions of the present invention as well as other desirable attribute thereof. Percentages of ingredients in Examples A-Y are weight/volume percents.

Examples A Through D

Table B provides formulations A through D and data related to those formulations.

TABLE B

| | Samples | | | |
|---|---|---|---|---|
| | A | B | C | D |
| Cilomilast | 0.2 | 0.2 | 0.0 | 0.05 |
| Sodium Chloride | 0.7 | 0.7 | 0.72 | 0.72 |
| Mannitol | 0.1 | None | None | None |
| Sorbitol | None | 0.1 | 0.15 | 0.15 |
| Boric Acid | 0.3 | 0.3 | 0.3 | 0.3 |

TABLE B-continued

| | Samples | | | |
|---|---|---|---|---|
| | A | B | C | D |
| Polyquaternium-1 | 0.0005 | 0.0005 | 0.001 | 0.001 |
| Sodium Hydroxide/HCl | None | None | pH 7.0 | pH 7.0 |
| Tromethamine*/HCl | pH 7.3 | pH 7.3 | None | None |

The four examples A through D illustrate the preservation efficacy of exemplary compositions of the present invention. The examples particularly illustrate the preservation efficacy of mannitol as used in the composition of the present invention. As can be seen, the composition containing mannitol met Ph. Eur. B criteria for A. Niger.

Examples E-J

Table C provides compositions E through J and data related to those formulations.

TABLE C

| Examples | | E | F | G | H | I | J |
|---|---|---|---|---|---|---|---|
| Cilomilast | | 0.2 | 0.2 | 0.2 | None | 0.2 | 0.2 |
| Sodium Chloride | | 0.7 | 0.7 | 0.7 | 0.74 | 0.7 | 0.7 |
| Mannitol | | 0.1 | 0.1 | 0.1 | 0.1 | 0.1 | 0.1 |
| Boric Acid | | 0.3 | 0.3 | 0.3 | 0.3 | 0.3 | 0.3 |
| Polyquaternium-1 | | 0.0005 | 0.0005 | 0.0005 | 0.0005 | 0.0005 | 0.0005 |
| Sodium Hydroxide/HCl | | pH 7.6 | pH 7.6 | None | None | None | None |
| Tromethamine*/HCl | | None | None | pH 7.6 | pH 7.6 | pH 7.6* | pH 7.3 |
| Purified Water | | QS 100% | QS 100% | QS 100% | QS 100% | QS 100% | QS 100% |
| A. Niger | 7 Days | 2.4 | 2.3 | 2.1 | 2.0 | 1.7 | 1.6 |
| | 14 Days | 2.1 | 2.6 | 2.2 | 2.1 | 2.0 | 1.9 |
| | 28 Days. | 2.1 | 2.1 | 1.7 | 1.8 | 1.9 | 1.7 |
| Candida A. | 7 Days | 1.9 | 2.1 | 2.0 | 2.1 | 2.0 | 1.7 |
| | 14 Days | 2.7 | 3.1 | 2.1 | 3.1 | 2.5 | 2.0 |
| | 28 Days. | 5.0 | 5.0 | 3.0 | 4.7 | 4.3 | 2.5 |
| S. Aureus | | 4.8 | 5.0 | 4.9 | 2.4 | 5.0 | 5.0 |
| | 24 Hours | 4.9 | 5.0 | 4.9 | 3.1 | 5.0 | 5.0 |
| | 7 Days | 4.9 | 5.0 | 4.9 | 4.9 | 5.0 | 5.0 |
| | 14 Days | 4.9 | 5.0 | 4.9 | 4.9 | 5.0 | 5.0 |
| | 28 Days | 4.9 | 5.0 | | | 5.0 | 5.0 |
| Psed. A | 24 Hours | 3.5 | 5.0 | 4.9 | 4.9 | 5.0 | 5.0 |
| | 7 Days | 5.0 | 5.0 | 4.9 | 4.9 | 5.0 | 5.0 |
| | 14 Days | 5.0 | 5.0 | 4.9 | 4.9 | 5.0 | 5.0 |
| | 28 Days. | 5.0 | 5.0 | 4.9 | 4.9 | 5.0 | 5.0 |
| | | 5.0 | 5.0 | | | 5.0 | 5.0 |
| E. Coli | 24 Hours | 4.9 | 4.9 | 4.8 | 4.3 | 4.9 | 4.9 |
| | 7 Days | 4.9 | 4.9 | 4.8 | 4.8 | 4.9 | 4.9 |
| | 14 Days | 4.9 | 4.9 | 4.8 | 4.8 | 4.9 | 4.9 |
| | 28 Days. | 4.9 | 4.9 | 4.8 | 4.8 | 4.9 | 4.9 |
| | | 4.9 | 4.9 | | | 4.9 | 4.9 |

*At least 0.28, 0.14, 0.28 and 0.2% tromethamine is used to adjust pH of example of G, H, and J, respectively.

TABLE B-continued

| | Samples | | | |
|---|---|---|---|---|
| | A | B | C | D |
| Purified Water | QS 100% | QS 100% | QS 100% | QS 100% |
| A. Niger 7 Days | 1.6 | 1.9 | 0.9 | 0.8 |
| 14 Days | 1.9 | 0.9 | 0.9 | 0.9 |
| 28 Days. | 1.7 | 0.9 | 0.7 | 0.6 |
| Candida A. 7 Days | 1.7 | 1.3 | 2.0 | 2.3 |
| 14 Days | 2.0 | 2.5 | 2.7 | 2.5 |
| 28 Days. | 2.5 | 3.7 | 4.3 | 3.0 |
| S. Aureus 24 Hours | 5.0 | 5.0 | 2.2 | 2.4 |
| 7 Days | 5.0 | 5.0 | 3.1 | 4.0 |
| 14 Days | 5.0 | 5.0 | 5.0 | 5.0 |
| 28 Days | 5.0 | 5.0 | 5.0 | 5.0 |
| | 5.0 | 5.0 | 5.0 | 5.0 |
| Psed. A 24 Hours | 5.0 | 5.0 | 5.0 | 3.0 |
| 7 Days | 5.0 | 5.0 | 5.0 | 4.0 |
| 14 Days | 5.0 | 5.0 | 5.0 | 5.0 |
| 28 Days. | 5.0 | 5.0 | 5.0 | 5.0 |
| | 5.0 | 5.0 | 5.0 | 5.0 |
| E. Coli 24 Hours | 4.9 | 4.9 | 3.7 | 4.2 |
| 7 Days | 4.9 | 4.9 | 5.1 | 5.1 |
| 14 Days | 4.9 | 4.9 | 5.1 | 5.1 |
| 28 Days. | 4.9 | 4.9 | 5.1 | 5.1 |
| | 4.9 | 4.9 | 5.1 | 5.1 |

*At least 0.2% tromethamine is used to adjust pH of example A and B.

The six examples E through J illustrate the high degree of preservation efficacy of compositions in accordance with the teaching of the present invention. Each of the compositions of examples E through J satisfies Ph. Eur. B Criteria.

Figure 2:
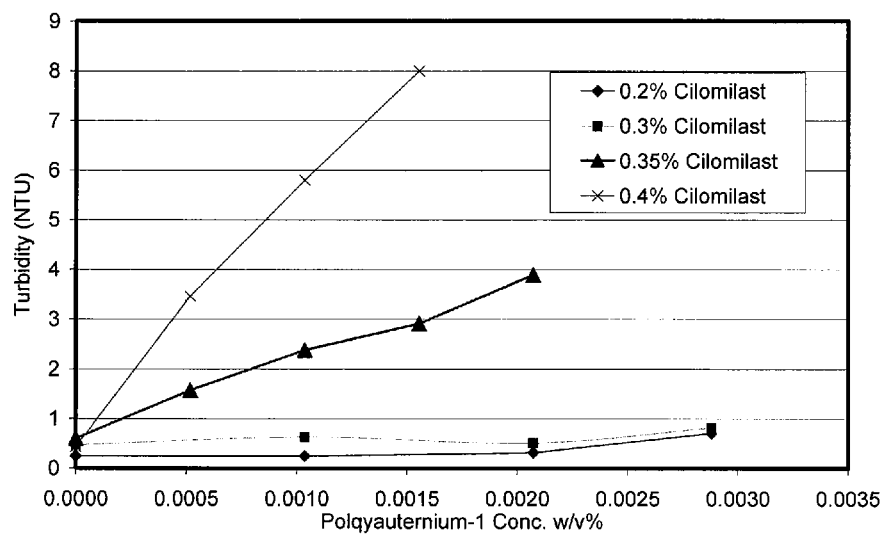
FIG. 2 is a chart showing level of turbidity for ophthalmic composition that include various amounts of antimicrobial agent and various amounts of therapeutic agent in the presence of 0.7 w/v % NaCl, 0.3 w/v % boric acid, 0.1 w/v % mannitol with pH adjusted to 7.6 with tromethamine.

With reference to FIG. 1 of the present invention, it is shown how compositions of the present invention that include sodium chloride concentration 0.4% (68 mmol) or higher avoid turbidity nephelos that might otherwise be associated with such cilomilast containing compositions. The graph in FIG. 2 shows that use of lower concentrations of polyquaternium-1 in conjunction with cilomilast produces less turbidity at a fixed concentration of sodium chloride.

Examples K-O

Table D provides compositions K through O and data related to those compositions.

TABLE D

| Example | K | L | M | N | O |
|---|---|---|---|---|---|
| Cilomilast | 0.2 | 0.2 | 0.2 | 0.2 | 0.2 |
| Sodium Chloride | 0.7 | 0.7 | 0.7 | 0.7 | 0.7 |
| Mannitol | None | None | None | None | 0.1 |
| Sorbitol | None | None | None | 0.1 | None |
| Propylene Glycol | None | None | 0.1 | None | None |

TABLE D-continued

| Example | | K | L | M | N | O |
|---|---|---|---|---|---|---|
| Glycerol | | None | 0.1 | None | None | None |
| Boric Acid | | 0.3 | 0.3 | 0.3 | 0.3 | 0.3 |
| Polyquaternium-1 | | 0.0005 | 0.0005 | 0.0005 | 0.0005 | 0.0005 |
| Tromethamine*/HCl | | pH 7.3 | pH 7.3 | pH 7.3 | pH 7.3 | pH 7.3 |
| Purified Water | | QS 100% | QS 100% | QS 100% | QS 100% | QS 100% |
| A. Niger | 7 Days | 1.4 | 1.8 | 1.6 | 1.9 | 1.6 |
| | 14 Days | 1.1 | 1.5 | 1.2 | 0.9 | 1.9 |
| | 28 Days. | 0.9 | 0.8 | 0.9 | 0.9 | 1.7 |

*At least 0.2% tromethamine is used to adjust pH of examples K through O.

The five examples K through O illustrate the superiority of mannitol when it is used as the polyol in the present invention as enhancement for preservation against A. Niger.

Examples P-T

Table E provides compositions P through T and data related to those compositions.

TABLE E

| Examples | | P | Q | R | S | T |
|---|---|---|---|---|---|---|
| Cilomilast | | 0.2 | 0.2 | 0.2 | 0.2 | 0.2 |
| Sodium Chloride | | 0.7 | 0.7 | 0.7 | 0.7 | 0.7 |
| Mannitol | | None | None | None | None | 0.1 |
| Sorbitol | | None | None | None | 0.1 | None |
| Propylene Glycol | | None | None | 0.1 | None | None |
| Glycerol | | None | 0.1 | None | None | None |
| Boric Acid | | 0.3 | 0.3 | 0.3 | 0.3 | 0.3 |
| Polyquaternium-1 | | 0.0005 | 0.0005 | 0.0005 | 0.0005 | 0.0005 |
| Tromethamine*/HCl | | pH 7.6 | pH 7.6 | pH 7.6 | pH 7.6 | pH 7.6 |
| Purified Water | | QS 100% | QS 100% | QS 100% | QS 100% | QS 100% |
| A. Niger | 7 Days | 1.7 | 2.0 | 1.6 | 1.6 | 2.2 |
| | 14 Days | 1.7 | 1.7 | 1.5 | 1.7 | 2.5 |
| | 28 Days. | 1.7 | 1.6 | 0.9 | 1.6 | 1.4 |
| A. Niger | 7 Days | 1.1 | 1.5 | 1.5 | 1.7 | 1.9 |
| | 14 Days | 1.0 | 1.4 | 1.6 | 1.6 | 1.9 |
| | 28 Days. | 1.0 | 1.1 | 1.5 | 1.5 | 1.9 |
| A. Niger | 7 Days | 1.4 | 1.5 | 1.6 | 1.4 | 1.8 |
| | 14 Days | 1.0 | 1.1 | 1.5 | 1.0 | 2.1 |
| | 28 Days. | 1.0 | 1.5 | 1.5 | 1.2 | 1.8 |

*At least 0.28% tromethamine is used to adjust pH of example P through T.

The five examples P through T again illustrate the superiority of mannitol when it is used as the polyol in the present invention as enhancement for preservation against A. Niger.

Examples U-X

Table F provides compositions U through X and data related to those compositions. These compositions have osmolality of about 290 mOsm/Kg.

TABLE F

| | | Examples | | | |
|---|---|---|---|---|---|
| | | U | V | W | X |
| Cilomilast | | 0.2 | 0.2 | 0.2 | 0.2 |
| Sodium Chloride | | 0.7 | 0.7 | 0.7 | 0.7 |
| Mannitol | | 0.1 | 0.1 | 0.1 | 0.1 |
| Boric Acid | | 0.3 | 0.3 | 0.3 | 0.3 |
| Polyquaternium-1 | | 0.0003 | 0.0004 | 0.0005 | 0.0006 |
| Sodium Hydroxide/HCl | | pH 7.6 | pH 7.6 | pH 7.6 | pH 7.6 |
| Purified Water | | QS 100% | QS 100% | QS 100% | QS 100% |
| A. Niger | 7 Days | 2.2 | 2.2 | 2.2 | 2.2 |
| | 14 Days | 1.9 | 1.9 | 1.6 | 1.8 |
| | 28 Days. | 1.8 | 1.8 | 1.8 | 1.8 |
| Candida A. | 7 Days | 1.6 | 1.2 | 1.6 | 1.3 |
| | 14 Days | 2.1 | 2.3 | 2.8 | 2.7 |
| | 28 Days. | 4.2 | 4.4 | 4.9 | 4.9 |
| S. Aureus | 6 Hrs | 5.1 | 5.1 | 5.1 | 5.1 |
| | 24 Hours | 5.1 | 5.1 | 5.1 | 5.1 |
| | 7 Days | 5.1 | 5.1 | 5.1 | 5.1 |
| | 14 Days | 5.1 | 5.1 | 5.1 | 5.1 |
| | 28 Days | 5.1 | 5.1 | 5.1 | 5.1 |
| Psed. A | 6 Hours | 4.4 | 5.0 | 4.6 | 4.6 |
| | 24 Hours | 5.0 | 5.0 | 5.0 | 5.0 |
| | 7 Days | 5.0 | 5.0 | 5.0 | 5.0 |
| | 14 Days | 5.0 | 5.0 | 5.0 | 5.0 |
| | 28 Days. | 5.0 | 5.0 | 5.0 | 5.0 |
| E. Coli | 6 Hours | 5.1 | 5.1 | 5.1 | 5.1 |
| | 24 Hours | 5.1 | 5.1 | 5.1 | 5.1 |
| | 7 Days | 5.1 | 5.1 | 5.1 | 5.1 |
| | 14 Days | 5.1 | 5.1 | 5.1 | 5.1 |
| | 28 Days. | 5.1 | 5.1 | 5.1 | 5.1 |

The five examples U through X illustrate the ability of the compositions of the present invention to exhibit desired preservation efficacy with lower concentrations of polyquaternium-1.

Example Y

Table G provides composition Y and data related to that composition.

TABLE G

| | | Composition Y |
|---|---|---|
| Cilomilast | | 0.2 |
| Sodium Chloride | | 0.55 |
| Mannitol | | 0.1 |
| Boric Acid | | 0.3 |
| Sodium Citrate Dihydrate | | 0.5 |
| Polyquaternium-1 | | 0.0005 |
| Sodium Hydroxide/HCl | | pH 7.6 |
| Tromethamine/HCl | | None |
| Purified Water | | QS 100% |
| A. Niger | 7 Days | 2.7 |
| | 14 Days | 2.5 |
| | 28 Days. | 1.9 |
| Candida A. | 7 Days | 0.4 |
| | 14 Days | 0.8 |
| | 28 Days. | <0.8 |
| S. Aureus | 6 Hours | 3.6 |
| | 24 Hours | 5.0 |
| | 7 Days | 5.0 |
| | 14 Days | 5.0 |
| | 28 Days | 5.0 |
| Psed. A | 6 Hours | 4.8 |
| | 24 Hours | 4.8 |
| | 7 Days | 4.8 |
| | 14 Days | 4.8 |
| | 28 Days. | 4.8 |
| E. Coli | 6 Hours | 4.8 |
| | 24 Hours | 4.8 |
| | 7 Days | 4.8 |
| | 14 Days | 4.8 |
| | 28 Days. | 4.8 |

While the compositions of the present invention can benefit from the osmolality provide by sodium citrate (e.g., sodium citrate dehydrate), as is shown in Table G, sodium citrate can also have some undesirable effects on preservation efficacy in certain formulations.

Table H below shows the effects of various excipients on turbidity of aqueous compositions that include 0.3 w/v % Cilomilast and 0.001 w/v % polyquaternium-1.

TABLE H

| Sample Component | Turbidity (NTU) | Visual Observation |
|---|---|---|
| 0.3% Cilomilast/0.001% polyquaternium-1 | 24 | hazy |
| Addition of following: | | |
| 0.35% NaCl | 6.2 | hazy |
| 0.7% NaCl | 0.90 | clear |
| 0.4% KCl | 14 | hazy |
| 0.6% KCl | 2.8 | clear |
| 0.8% KCl | 1.8 | clear |
| 0.1% sodium citrate | 5.6 | hazy |
| 0.2% sodium citrate | 2.6 | clear |
| 0.4% sodium citrate | 2.2 | clear |
| 0.8% sodium citrate | 1.9 | clear |
| 0.2% sodium sulfate | 7.2 | hazy |
| 0.4% sodium sulfate | 1.9 | clear |
| 0.8% sodium sulfate | 2.0 | clear |
| 0.8% Tromethamine | 1.2 | clear |
| 0.8% $MgCl_2$ | 70 | hazy |
| 0.4% sodium propionate | 32 | hazy |
| 0.8% sodium propionate | 25 | hazy |
| 0.8% disodium phosphate | 6.3 | hazy |
| 0.6% Boric acid | 24 | hazy |
| 1.2% Boric acid | 13 | hazy |
| 0.45% Boric Acid, 1.5% Sorbitol | 19 | hazy |
| 0.6% Boric Acid., 2% Sorbitol | 18 | hazy |
| 0.3% Cilomilast/0.00025% polyquaternium-1 | 18.7 | hazy |
| 4% Sorbitol | 10 | hazy |

I claim:

1. An aqueous ophthalmic composition, comprising:
an anionic therapeutic agent;
mannitol at a concentration that is at least 0.05 w/v % but is no greater than 1.5 w/v %;
borate at a concentration that is at least 0.1 w/v % but is no greater than 0.5 w/v %;
sodium chloride a concentration that is at least 85 mmol wherein the sodium chloride enhances the physical stability or clarity of the composition;
a positively charged antimicrobial agent that is a polymeric quaternary ammonium compound; and
water, wherein the osmolality of the ophthalmic composition is in the range of 240 to 360 mOsm/kg and wherein the composition is an aqueous solution having a turbidity of less than 2 NTU.

2. An aqueous ophthalmic composition as in claim 1 wherein the anionic therapeutic agent includes a negatively charged carboxylic acid group at a pH that is from about 5 to about 9.

3. An aqueous ophthalmic composition as in claim 1 wherein the therapeutic agent is a PDE-4 inhibitor.

4. An aqueous ophthalmic composition as in claim 1 wherein the therapeutic agent is cilomilast.

5. An aqueous ophthalmic composition as in claim 1 wherein the mannitol is at a concentration that is at least 0.08 w/v % but is no greater than 0.12 w/v %.

6. An aqueous ophthalmic composition as in claim 1 wherein the positively charged antimicrobial agent is present in the composition at a concentration that is at least 0.0001 w/v % but is no greater than 0.0012 w/v %.

7. An aqueous ophthalmic composition as in claim 1 wherein the antimicrobial agent is polyquaternium-1.

8. An aqueous ophthalmic composition as in claim 7 wherein the antimicrobial agent is present in the composition in a concentration that is at least 0.0001 w/v % but is no greater than 0.0012 w/v %.

9. An aqueous ophthalmic composition as in claim 1 wherein the composition satisfies Ph. Eur. A, Ph. Eur. B or both.

10. An aqueous ophthalmic composition as in claim 1 wherein the composition is substantially free of any benzalkonium chloride.

11. An aqueous ophthalmic composition as in claim 1 wherein the therapeutic agent includes an acidic group that exhibits a negative charge at a pH in the range of 5 to 9.

12. An aqueous ophthalmic composition as in claim 1 wherein the concentration of borate is no greater than 0.4 w/v % and the concentration of mannitol is no greater than 0.2 w/v %.

13. An aqueous ophthalmic composition as in claim 1 wherein the composition is substantially free of any surfactant.

14. An aqueous ophthalmic composition as in claim 1 wherein the composition is entirely free of any surfactant.

15. An aqueous ophthalmic composition as in claim 1 wherein the pH of the ophthalmic composition is about 6 to about 8.

16. An aqueous ophthalmic composition as in claim 1 wherein the concentration of the therapeutic agent is at least 0.01 w/v % and no greater than 0.5 w/v %.

17. An aqueous ophthalmic composition as in claim 1 wherein the therapeutic agent is cilomilast and the concentration of the therapeutic agent is at least 0.01 w/v % and no greater than 0.3 w/v %.

18. An aqueous ophthalmic composition as in claim 1 wherein the sodium chloride is present in the composition at a concentration that is at least 100 mmol.

19. An aqueous ophthalmic composition, comprising:
an anionic therapeutic agent wherein the concentration of the therapeutic agent is at least 0.01 w/v % and no greater than 0.5 w/v %;
mannitol at a concentration that is at least 0.05 w/v % but is no greater than 1.5 w/v %;
borate at a concentration that is at least 0.1 w/v % but is no greater than 0.5 w/v %;
a positively charged antimicrobial agent that is a polymeric quaternary compound wherein the positively charged antimicrobial agent is present in the composition in a concentration that is at least 0.0001 w/v % but is no greater than 0.0012 w/v %;
osmolality enhancing agent wherein the osmolality enhancing agent raises the osmolality of the ophthalmic composition at least 160 mOsm/Kg relative to a control composition that includes the exact same ingredients as the ophthalmic composition with the exception that the osmolality enhancing agent is replaced with water and pH is brought to the same value as that of the ophthalmic composition by using sodium hydroxide or hydrogen chloride if necessary and wherein the osmolality enhancing agent is present in the composition at a concentration that is at least 110 mmol but no greater than no greater than 200 mmol and wherein the osmolality enhancing agent also enhances the physical stability or clarity of the composition; and
water;
wherein the osmolality of the ophthalmic composition is in the range of 240 to 360 mOsm/kg and wherein the composition is substantially free of any benzalkonium chloride and wherein the osmolality enhancing agent is sodium chloride and wherein the composition is an aqueous solution having a turbidity of less than 2 NTU.

20. An aqueous ophthalmic composition as in claim 1 wherein the borate is boric acid.

21. An aqueous ophthalmic composition as in claim 19 wherein the borate is boric acid and wherein the anionic therapeutic agent includes a negatively charged carboxylic acid group at a pH that is from about 5 to about 9.

22. An aqueous ophthalmic composition, comprising:
- an anionic therapeutic agent wherein the concentration of the therapeutic agent is at least 0.01 w/v % and no greater than 0.5 w/v %;
- mannitol at a concentration that is at least 0.05 w/v % but is no greater than 1.5 w/v %;
- borate at a concentration that is at least 0.1 w/v % but is no greater than 0.5 w/v %;
- a positively charged antimicrobial agent that is a polymeric quaternary ammonium compound wherein the positively charged antimicrobial agent is present in the composition in a concentration that is at least 0.0001 w/v % but is no greater than 0.0012 w/v %;
- osmolality enhancing agent that is entirely or substantially entirely sodium chloride wherein the osmolality enhancing agent is present in the composition at a concentration that is at least 110 mmol but no greater than no greater than 200 mmol and wherein the osmolality enhancing agent also enhances the physical stability or clarity of the composition; and
- water;
- wherein the osmolality of the ophthalmic composition is in the range of 240 to 360 mOsm/kg and wherein the composition is substantially free of any benzalkonium chloride and wherein the osmolality enhancing agent is sodium chloride and wherein the composition is an aqueous solution having a turbidity of less than 2 NTU.

23. An aqueous ophthalmic composition as in claim 22 wherein the therapeutic agent includes an acidic group that exhibits a negative charge at a pH in the range of 5 to 9.

24. An aqueous ophthalmic composition as in claim 19 wherein the osmolality enhancing agent is entirely sodium chloride.

* * * * *